Figure 1:

United States Patent [19]

Kratky et al.

[11] 4,170,128

[45] Oct. 9, 1979

[54] APPARATUS FOR DENSITY DETERMINATION

[76] Inventors: Otto Kratky, Drosselweg 15; Hans Leopold, August-Musgergasse 4, both of A-8010 Graz; Hans Stabinger, Peterstalstrasse 156, A-8042 Graz, all of Austria

[21] Appl. No.: 855,804

[22] Filed: Nov. 29, 1977

[30] Foreign Application Priority Data

Nov. 29, 1976 [AT] Austria ................................ 8831/76

[51] Int. Cl.² .............................................. G01N 9/00
[52] U.S. Cl. .......................................... 73/30; 73/32 A
[58] Field of Search ............ 73/32 A, 32 R, DIG. 1, 73/30

[56] References Cited

U.S. PATENT DOCUMENTS 2,943,476  7/1960  Bernstein .......................... 73/32 A
3,585,843  6/1971  Stansfeld .......................... 73/32 A

FOREIGN PATENT DOCUMENTS 2249269  4/1974  Fed. Rep. of Germany .......... 73/32 A Primary Examiner—James J. Gill
Attorney, Agent, or Firm—Martin A. Farber

[57] ABSTRACT

An apparatus for measurement of density, particularly of liquids and gases, by determination of the characteristic frequency of a tube-shaped bending-type oscillator which is filled with the measuring substance, which oscillator is connected with a tensioned body, the tension of which is dependent upon the temperature and/or the pressure of the measuring substance. The tensioned body is bending-slack (a string). A member is provided which guarantees that the deflection of the bending oscillator is transmitted to the string and the restoring force of the string is transmitted to the oscillator.

12 Claims, 6 Drawing Figures

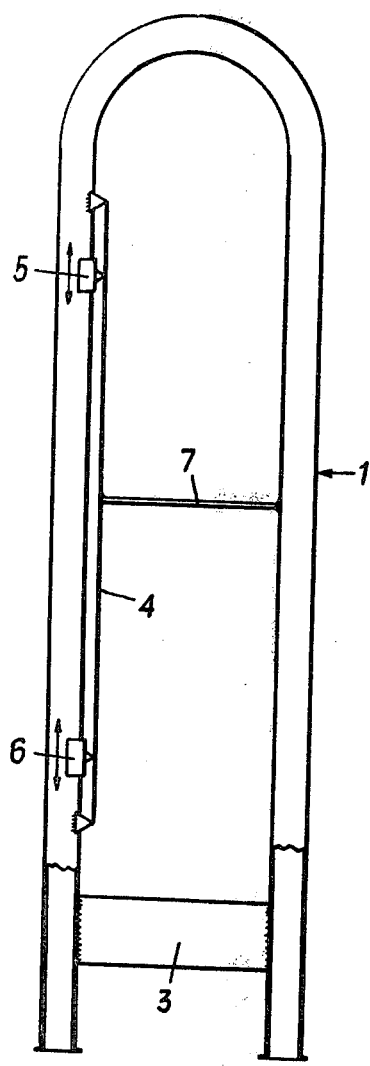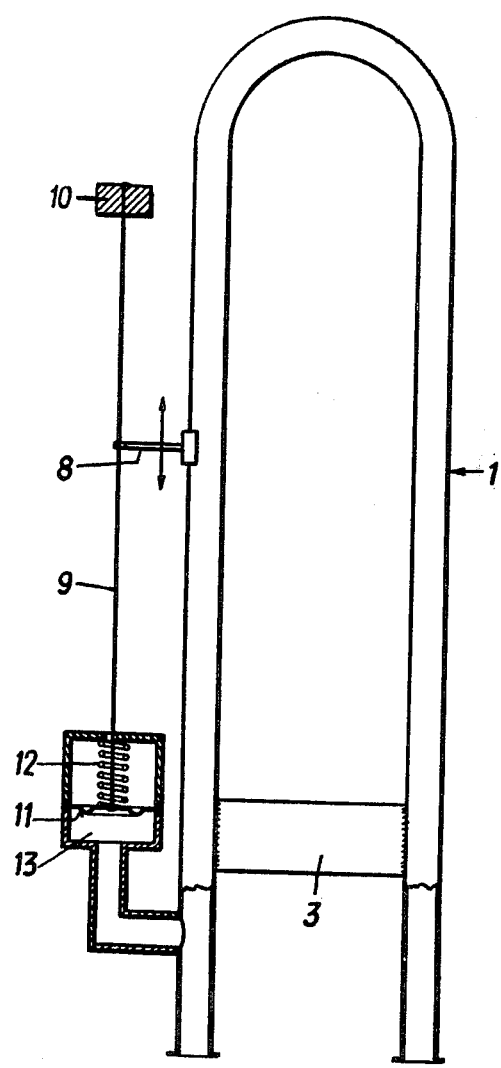

APPARATUS FOR DENSITY DETERMINATION

The invention relates to an apparatus for the measurement of the density, particularly of liquids and gases, by the determination of the characteristic frequency of a tube-shaped bending-type oscillator which is filled with the measuring substance, which oscillator is connected with a tensioned body, the tension of which is dependent upon the temperature and, respectively, or on the pressure for the measuring substance. It relates first of all to arrangements by which a mechanical-electrical transformer which is influenced by the bending-type oscillator is connected via an electronic device with an electro-mechanical transducer which influences the bending-type oscillator.

In Austrian Pat. No. 280,662 there is described an apparatus for the measurement of density, particularly of liquids and gases, by which the measurement of the density is attributed to the determination of the period of oscillation of a bending-type oscillator which is filled with the substance to be measured and which is excited in an electrical manner to its resonant frequency.

The bending oscillator is constructed in the form of a U-shaped tube, which is rigidly held at its open ends. The tube can be excited in two different oscillating forms, namely normal to the plane of the U or in the plane of the U, whereby the legs oscillate counter to one another (FIGS. 1 to 4). The resonant circuit frequency $\omega$ of such a bending-type oscillator permits calculation of $$\omega = \sqrt{c/m}., \tag{1}$$

where c is the constant of elasticity (or spring constant) and m is the mass of the oscillator.

The value of the constant of elasticity if determined by the modulus of elasticity of the oscillator material, the dimensions of the oscillator and the form of the oscillation. The mass m comprises the mass $M_o$ of the empty oscillator and the mass $\rho \cdot V$ of the preparation, whereby $\rho$ signifies its density and V signifies that volume of the preparation which participates in the oscillation. This volume is given by the dimensions of the oscillator and the position of the oscillating nodes. From this it follows:

$$\omega = \sqrt{\frac{c}{M_o + \rho V}} \tag{2}$$

$$\frac{1}{\omega^2} = \frac{1}{c} \cdot (M_o + \rho V) \tag{3}$$

$$\rho = \frac{1}{\omega^2} \cdot \frac{c}{V} - \frac{M_o}{V} \tag{4}$$

If the oscillator is filled successively with two different substances of known density and the corresponding resonant frequencies are measured, the oscillation-dependent magnitudes c/v and $M_o/V$ can be determined. Since these magnitudes may be considered as apparatus constants, they can be used for calculation of the density of an unknown liquid, in the manner that one fills the latter in the oscillator and now measures the characteristic frequency or eigenfrequency.

Now the magnitudes c and V are dependent on the temperature and on the pressure of the measuring product, since the modulus of elasticity of the tube material is temperature dependent and the dimensions of the oscillating tube are changed by pressure and temperature.

In German Offenlegeschrift No. 2,249,269 a method is set forth to compensate this dependency by controllably influencing the temperature dependency of the constant of elasticity of the oscillator. For this purpose the measuring oscillator is fastened or braced via strong springs, whereby a change of the characteristic frequency is achieved, which is proportional to the force applied by the springs. If now the springs and the measuring oscillator are accomodated in the same housing, then the temperature of the springs is influenced by the temperature of the preparation which flows through the measuring oscillator. In the ideal case—with sufficiently long adaptation time—the springs assume the temperature of the preparation. Since the elasticity or elastic force is lowered with increasing temperature, as a result of the temperature dependency of the modulus of elasticity, a characteristic frequency change occurs which results from the temperature dependent fastening or bracing of the measuring oscillator, which change acts opposite to the temperature dependent characteristic frequency change of the oscillator parameters (c and V). With corresponding dimensioning these influences can be compensated. Since for the compensation only the change of an existing fastening or bracing is used by the springs, temperature coefficient of the modulus of elasticity lies yet at the order of magnitude of only $22.10^{-4}$ per °C., the compensation springs must be pretensioned with large forces, so that the temperature dependent portions are sufficiently large. These springs require large forces, which springs are wound from thick wire. Since the compensation springs form the temperature detector for the compensation, the system only can function when the measuring oscillator (which assumes the temperature of the preparation which flows therethrough) and the compensation springs have the same temperature. The allowable temperature difference, depending upon the accuracy which is required, is permitted only to amount to only several hundreth of a degree. With the method set forth in German Offenlegeschrift No. 2,249,269, the last-mentioned requirement practically cannot be realized since the springs are tempered only over the gas atmosphere of the space in which the measurement oscillator lies. The temperature of this space, however in addition to the preparation temperature, also is still strongly influenced by the temperature of the housing and consequently by the environment or ambient temperature. Apart from this the large heat capacity of the strong springs prevents a quick temperature adaptation or adjustment to a changing preparation temperature, whereby this system is not able to be used for measurements with temperature change speeds which are customary in industrial processes.

It is an object of the present invention to influence the constant of elasticity c of the measuring oscillator by means of an apparatus which does not have the above-mentioned disadvantages.

For this in accordance with the present invention with a device of the introductory mentioned type, the tensioned body is bending-slack (a string or cord), whereby means are provided which guarantee that the deviation or deflection movement of the bending oscillator is transmitted or applied to the cord and the restoring force of the cord is transmitted or applied to the bending oscillator.

The bending-type oscillator thereby is connected with the stretched or tensioned cord such that the restoring force of the cord is added to the restoring force of the oscillator. Since the restoring force of the cord is proportional to the cord tension and inversely proportional to the cord length, out of this measure there results an elasticity or elastic force of the oscillator, which elasticity or elastic force is able to be controlled by the tension of the cord. If the cord tension is made dependent on the temperature of the preparation, the temperature influence may be compensated. A pressure-dependent cord tension yields a pressure compensation. An inertialess temperature-dependent change of the cord tension can be achieved in accordance with the invention in the manner that the cord (thermal coefficient of expansion small) is secured on the oscillator tube such that thermal expansion of the oscillator more or less stretches or tensions the cord. The exact adjustment or adaptation to the amount of the dependency to be compensated is thereby provided by variation of the length of the cord.

Further details of the invention result on the basis of the drawing, in which among other things two embodiment examples are illustrated.

Figure 2:
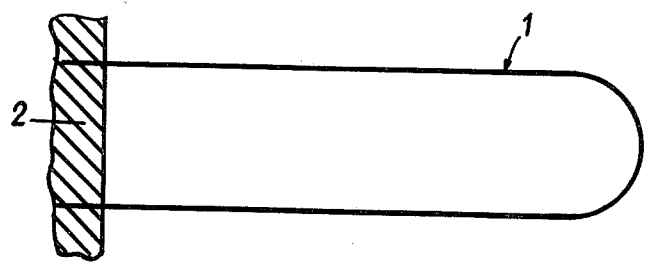
Figure 3:
Figure 4:
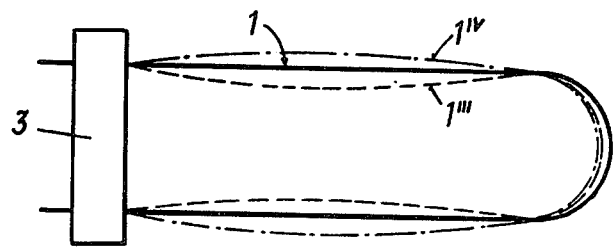

FIG. 1 shows a side of a U-shaped bending-type oscillator which is excited for oscillating perpendicular to the plane of the U, FIG. 2 is a plan view thereof, FIG. 3 is a side view of a U-shaped bending-type oscillator which is excited to oscillations in the plane of the U, FIG. 4 is a plan view thereof, FIG. 5 is an embodiment example of the invention for the temperature compensation, and FIG. 6 is an embodiment example for pressure compensation.

The FIGS. 1 and 2 show a U-shaped bending-type oscillator 1, the leg ends of which are held or clamped in a holder 2 and which is excited into oscillations perpendicularly to the plane of the U, as that is indicated by the dot-dashed lines 1', 1'' in FIG. 1.

To the contrary FIGS. 3 and 4 show a U-shaped bending-type oscillator 1, with a yoke or crossbar 3 secured on the legs, which oscillator is excited in the plane of the U, as this is illustrated by the dot-dashed lines 1'' and the dot-dashed lines 1 IV.

With the embodiment of the invention illustrated in FIG. 5, which is provided for the temperature compensation, the U-shaped oscillating tube 1 oscillates in the plane of the U. The legs oscillate counter to one another as evident from FIG. 4. A string or cord 4 is stretched or mounted along one leg, the effective length of which can be adjusted by displacement of the slides 5, 6. The center of the cord 4 is connected with the opposite leg via a rod 7. If now the U-shaped oscillator tube oscillates in the plane of the U (FIG. 4), then the cord 4 deflects or deviates by means of the oscillating movement of the legs and the restoring force of the cord is added to the restoring force of the legs, since the two holding or clamping positions of the cord move in opposite direction than its center. The linear, thermal coefficient of expansion of the cord 4 is substantially smaller than that of the oscillator material. In this manner the cord 4 is stretched or tensioned stronger with a temperature increase, its restoring force correspondingly rises and equalizes or compensates the decrease of the restoring force of the oscillator 1 which is attributed to the temperature-conditioned reduction of the modulus of elasticity of the oscillator material.

In comparison to the previously known devices, a decisive advantage of this construction is that the oscillator tube itself constitutes the temperature detector for the compensation. A temperature change is thus measured with that element of the system on which the change to be compensated occurs, whereby a completely delay-free compensation is attained. This circumstance is of the greatest importance with the use of the device in closed control circuits, since the disturbing variable "temperature" is negligible and quick—practically inertialess operating—controllers can be realized. By the use of cords or strings made of materials with the coefficient of expansion of practically zero (invar, quartz, Wolfram or tungsten), their temperature, which is determined by the atmosphere of the space surrounding the measuring oscillator, has no disturbing influence on the measurement.

The cord of the length l—assumed bending-slack—is an exact transducer or converter from the tensile force S to the constant of elasticity c.

$$c = 4S/l$$

The cord tension S of a bending-slack or flexing-slack cord with the coefficient of expansion zero secured on an oscillator tube which has a coefficient of expansion $\alpha$ (for example, steel $1.6 \times 10^{-5}/K$), for a temperature change of the oscillating tube $\theta$ results to $$S = \alpha \cdot E \cdot \theta \cdot F$$

whereby F is the cross-section and E is the modulus of elasticity of the cord. According to the above, consequently, the constant of elasticity of the cord is directly proportional to the temperature variation $\theta$. Since the cord equation is valid from the tensile stress zero on, no nominal value clamping of the cord is necessary. Thus the cross-section of the cord can be held very small. (For a steel oscillator of the wall thickness 0.2 mm with a diameter of 7 mm, the necessary cord cross-section amounts to 0.03 mm$^2$).

It is particularly advantageously achieved that the cord compensation practically serves the entire additionally applied elasticity or elastic force of the compensation, whereas with the subject matter according to German Offenlegeschrift No. 2,249,269 only a very small part of the effective applied elastic force which in its entire magnitude acts detuned or off-resonance is available for the temperature compensation. Undesired variations or changes on the compensation system (aging, tolerances in the mechanical formations) influence the measurement precision thus be several orders of magnitude greater than with the cord.

With the embodiment example of the invention as illustrated in FIG. 6, the oscillator 1 is connected with the cord 9 via a rod 8, which cord is fixed on one end 10 and is connected with a membrane 11 on the other end. The cord 9 is pretensioned or prestretched by means of a spring 12. A pressure change in the space 13 which stands in communication with the preparation changes the tension of the cord and consequently the restoring force of the oscillator. The rod 8 can be shifted along the cord 9 for adjustment of the compensation.

A certain temperature compensation can also additionally be achieved under the circumstances if necessary in the manner that for the rod 7 (FIG. 5) a material is selected, the thermal coefficient of expansion of which differs from that of the oscillator material.

We claim:

1. An apparatus for the measurement of the density of a fluid, by the determination of the characteristic frequency of a vibrating tube filled with said fluid, comprising:

a tube-shaped element filled with said fluid;

means for vibrating said element transverse to its longitudinal axis;

an elongate relatively thin pretensioned body;

means for varying the tension in said body in response to a characteristic of said fluid;

means for transmitting the deflection of the tube-shaped element to a deflection of part of said body, and the force of said body resisting deflection to said element.

2. The apparatus as set forth in claim 1, wherein said body in a cord.

3. The apparatus according to claim 1, wherein the two ends of said body are fastened to said tube-shaped element.

4. The apparatus as set forth in claim 3, wherein said tube-shaped element is U-shaped having two legs, said body is connected at said two ends to one of said legs on a side thereof facing the other of said legs, a rod is connected to said body and to said other leg of said tube-shaped element, and two slides are moveably disposed on said one leg and each have a portion contacting said body, each of said two slides, respectively, is disposed adjacent opposite ends of said body relative to said rod.

5. The apparatus according to claim 1, further comprising slide means moveably disposed on said tube-shaped element adjacent said body, at least one rod connected to said body, said slide means and said at least one rod, respectively, for varying the effective length of said body.

6. The apparatus according to claim 5, wherein said tube-shaped element is made of a material having a different thermal coefficient of expansion than the thermal coefficient of expansion of said body 7. The apparatus according to claim 5, wherein said tube-shaped element is made of a material having a different thermal coefficient of expansion than the thermal coefficient of expansion of said at least one rod.

8. The apparatus according to claim 5, wherein said tube-shaped element is made of a material having a different thermal coefficient of expansion than the thermal coefficient of expansion of said body and said at least one rod.

9. The apparatus as set forth in claim 5, wherein said at least one rod at one end thereof is connected to said tube-shaped element and at another end thereof is connected centrally to said body, said slide means constitute two slides each having a portion contacting said body.

10. The apparatus according to claim 1, wherein said means for varying comprises means for tensioning said body dependent on the pressure of said fluid.

11. The apparatus as set forth in claim 10, wherein said body is fixed on one end thereof, a slide moveably mounted on said tube-shaped element, a rod having ends respectively connected to said slide and moveably to said body, said tensioning means comprises a membrane connected to the other end of said body and communicating with said fluid in said tube-shaped body.

12. The apparatus as set forth in claim 11, further comprising a cylinder, said membrane is mounted in said cylinder, spring means engaging one side of said membrane for prestressing said body, a conduit communicatingly connected to said cylinder at the other side of said membrane and to said tube-shaped element.

* * * * *